(12) United States Patent
Sugiura (10) Patent No.: US 8,470,374 B2
(45) Date of Patent: Jun. 25, 2013

(54) GRANULAR ANTIMICROBIAL AGENT FOR WATER PROCESSING

(75) Inventor: Koji Sugiura, Nagoya (JP)

(73) Assignee: Toagosei Co., Ltd., Tokyo (JP)

( * ) Notice: Subject to any disclaimer, the term of this patent is extended or adjusted under 35 U.S.C. 154(b) by 0 days.

(21) Appl. No.: 13/384,095

(22) PCT Filed: Jul. 14, 2010

(86) PCT No.: PCT/JP2010/061892
§ 371 (c)(1),
(2), (4) Date: Jan. 13, 2012

(87) PCT Pub. No.: WO2011/007798
PCT Pub. Date: Jan. 20, 2011

(65) Prior Publication Data
US 2012/0128790 A1    May 24, 2012

(30) Foreign Application Priority Data

Jul. 16, 2009    (JP) .................................. 2009-167442

(51) Int. Cl.
*A61K 9/14*    (2006.01)
(52) U.S. Cl.
USPC ........................................................ 424/489
(58) Field of Classification Search
None
See application file for complete search history.

(56) References Cited

U.S. PATENT DOCUMENTS

| | | | |
|---|---|---|---|
| 2005/0064193 A1* | 3/2005 | Fechner et al. | 428/406 |
| 2006/0127498 A1 | 6/2006 | Sugiura | |
| 2007/0186587 A1 | 8/2007 | Dennert | |

FOREIGN PATENT DOCUMENTS

| | | |
|---|---|---|
| JP | 1-313531 A | 12/1989 |
| JP | 2-302451 A | 12/1990 |
| JP | 3-83905 A | 4/1991 |
| JP | 4-166289 A | 6/1992 |
| JP | 6-126285 A | 5/1994 |
| JP | 6-190369 A | 7/1994 |
| JP | 7-25635 A | 1/1995 |
| JP | 7-48142 A | 2/1995 |
| JP | 09322927 A * | 12/1997 |
| JP | 2004-262763 A | 9/2004 |
| JP | 2005-314292 A | 11/2005 |
| JP | 2006-520311 A | 9/2006 |
| JP | 2008-214131 A | 9/2008 |
| JP | 2008-279056 A | 11/2008 |
| WO | WO 2005/087675 A1 | 9/2005 |

OTHER PUBLICATIONS

International Search Report Issued in PCT/JP2010/061892, dated Sep. 7, 2010.

* cited by examiner

*Primary Examiner* — Susan Tran
(74) *Attorney, Agent, or Firm* — Birch, Stewart, Kolasch & Birch, LLP (57) ABSTRACT

[Object] The object of the invention is to provide a granular antimicrobial agent for water processing which has sufficient water permeability and antimicrobial effect, and the effective duration of which can be readily ascertained when used as a water-processing antimicrobial agent in the home.
[Means for Solving the Problems] A granular antimicrobial agent for water processing which has a solubility at 25° C. of preferably 0.1 mg/g·L·hour to 1 mg/g·L·hour, comprises 0.5 wt % to 4 wt % of $Ag_2O$, 2 wt % to 10 wt % of $K_2O$, 35 wt % to 50 wt % of $SiO_2$, and 40 wt % to 55 wt % of $B_2O_3$, and has a semispherical or conical shape in part was found. In addition, the inventors found that the antimicrobial agent is highly suitable for use in various kinds of water processing, particularly, the antimicrobial treatment of water used for washing, and completed the invention.

10 Claims, 4 Drawing Sheets

GRANULAR ANTIMICROBIAL AGENT FOR WATER PROCESSING

TECHNICAL FIELD

The present invention relates to a granular antimicrobial agent for water processing, in which antimicrobial glass, which is composed of specific components having adjusted solubilities, is adjusted into a specific shape, which is excellent in terms of the water permeability, and the effective duration of which can be easily determined. The granular antimicrobial agent for water processing of the invention is excellent in terms of the water permeability, excellently exhibits an antimicrobial effect, and either allows passage of water that is to undergo an antimicrobial treatment or is dipped in water that is to undergo an antimicrobial treatment so as to exhibit an effect of efficiently reducing the number of microbes included in the water. In addition, the granular antimicrobial agent for water processing itself is dissolved, and the amount thereof is reduced, whereby anyone can readily ascertain the effective duration of the antimicrobial effect. The granular antimicrobial agent for water processing of the invention can be particularly preferably used for antimicrobial treatments of water used for washing.

BACKGROUND ART

Hitherto, silver, copper, and other antimicrobial metals supported in apatite, zeolite, glass, zirconium phosphate, silica gel, or the like have been known as inorganic antimicrobial agents. In comparison to organic antimicrobial agents, these inorganic antimicrobial agents have high safety and do not volatilize or decompose, thus having characteristics of a long-lasting antimicrobial effect and excellent heat resistance. Therefore, antimicrobial resin compositions obtained by mixing the antimicrobial agents and a variety of polymer compounds are used for a variety of uses in the form of antimicrobial-processed products that are processed into a fibrous shape, a film shape, a variety of compacts, and the like.

Among them, a vitreous antimicrobial agent containing antimicrobial metals, such as silver, copper, and zinc, that is, antimicrobial glass is mixed in antimicrobial resin compositions for a variety of uses and used taking advantage of the characteristics that the granularity of the glass, the refractive index, the elution properties of the antimicrobial metals, and the like can be easily controlled according to the purpose (for example, refer to Patent Literature 1, 2, and 3).

12 mesh (aperture size 1.68 mm)-passable particulates that are used to inhibit the generation of aquatic microbes, such as slime and algae that generate in cooling towers, water tanks, pools, solar systems, irrigation water, and the like (for example, refer to Patent Literature 4), antimicrobial flake-shaped glass that is used as a paint or lining materials for painting water-processing facilities, livestock-producing facilities, food factories, and building materials, or a reinforcing filler of resin compacts, such as air conditioners, and the like so as to effectively inhibit the generation and propagation of microbes, fungus, and algae at the corresponding sites (for example, refer to Patent Literature 5), borate-based or phosphate-based water-soluble silver glass which is used to suppress the propagation and sterilize microorganisms, such as microbes, filamentous fungi, yeast, and algae, that propagate in water inside tanks used in ultrasonic humidifiers, which is made into a bead shape or a certain form that is maintained and used in water inside tanks, and which uniformly contains monovalent silver ions (for example, refer to Patent Literature 6), glass particles with a particle diameter of 1 mm to 50 mm which are filled in a column installed in a water-supplying system or a circulating system of an apparatus for purifying bathwater, and through which bathwater passes (for example, refer to Patent Literature 7), silver ion-containing soluble glass powders with a dissolution rate of 0.005 mg/g/Hr to 50 mg/g/Hr which are accommodated in a cartridge filter for obtaining deodorized and sterilized potable water and the like used in restaurants, houses, and the like are suggested as the vitreous antimicrobial agent for water processing.

Furthermore, a method in which an antimicrobial agent is brought into contact with water used for washing that is supplied to a washing tub so as to supply, for example, silver ion-based antimicrobial components to the washing tub in order to suppress the generation of bad odors of laundry, such as clothes (for example, refer to Patent Literature 9), and antimicrobial glass for carrying out an antimicrobial treatment using silver ions during or after washing of articles to undergo an antimicrobial treatment in which the maximum diameter (t1) is within a range of 1 mm to 50 mm, and the amount of eluted silver ions is within a range of 0.5 mg/(g·24 Hrs) to 100 mg/(g·24 Hrs) (for example, refer to Patent Literature 10) are known as antimicrobial agents for washing. However, the antimicrobial glass has a problem of discoloration, and Patent Literature 10 suggests using at sites which are not visible or coating with a colored coating material as the countermeasures. When the antimicrobial glass is installed so as not to be visible, it is difficult for general consumers to ascertain the effective duration (service life) of the antimicrobial agent, and, even when the antimicrobial agent is installed so as to be visible, it is necessary for the antimicrobial agent itself to exhibit an appropriate change in appearance in order to allow general consumers to ascertain the effective duration of the antimicrobial agent by a simple method of measuring by hand, checking the appearance, or the like but there has been no technique that is intended to allow general consumers to ascertain the effective duration (service life) by a simple method.

Methods of manufacturing silver glass that elutes silver ions and can be used as antimicrobial glass include a method of manufacturing granular glass having an average particle diameter of 0.1 μm to 10 mm (for example, refer to Patent Literature 11), a method of manufacturing silver ion-containing glass for which an alkali metal salt of boric acid is used as the raw material (for example, refer to Patent Literature 11), and the like, but these methods are not intended to allow general consumers to ascertain the effective duration (service life) by a simple method.

In the case of use in water-processing, when a powdered antimicrobial agent is used, generally, there are problems in that the water becomes muddy, and thus cannot be recovered. Therefore, granular products are preferred as a water-processing antimicrobial agent. However, silver glass obtained by manufacturing methods according to the general conventional art has a cullet form (crushed glass) or a flake shape and an uneven granularity or shape, and thus, in practice, there is room for further improvement when the silver glass is packed in a bag and used, such as the filling properties, the risk of scratching and the like due to sharp-edge portions, the tearing of the bag during processing and use, furthermore, the susceptibility to clogging caused by an increase in the filling density which leads to degradation of the water permeability, and the like. Meanwhile, fusion molding can also be used to make the glass into a certain shape, such as glass beads, but the costs for the molding process are high, and there is a limitation on the shapeable glass compositions, and therefore it is difficult to obtain a uniform molded product in a glass composition having an appropriate solubility.

Considering the applications in the home, such as the provision of microbe resistance and deodorization of water used for washing, the provision of microbe resistance to bathwater, and the inhibition of algae growth in a water tank, the appropriate amount of the antimicrobial agent used is several tens of grams per each use for the handling properties or detection of the service life. Antimicrobial products obtained by filling several tens of grams of the antimicrobial agent in a knitted fabric, non-woven fabric, or other bag can be preferably used for the above uses, and the effective duration can be easily determined by detection of the appearance or measuring by hand. When the particles of the antimicrobial agent do not allow passage of water when manufacturing such a product, it is difficult to obtain the antimicrobial effect. In addition, when the weight of one particle is more than 1 gram, there are problems in that it is difficult to adjust the amount of the antimicrobial agent filled in a bag to be constant, a large variation is caused in the amount of the antimicrobial agent filled by an automatic filling machine, and the like. There has been no example of silver glass that is appropriate for the use of water processing.

CITATION LIST

Patent Literature

[Patent Literature 1] JP-A-2004-262763 (JP-A denotes a Japanese unexamined patent application publication.)
[Patent Literature 2] JP-A-01-313531
[Patent Literature 3] JP-A-02-302451
[Patent Literature 4] JP-A-03-83905
[Patent Literature 5] JP-A-07-25635
[Patent Literature 6] JP-A-06-190369
[Patent Literature 7] JP-A-06-126285
[Patent Literature 8] JP-A-04-166289
[Patent Literature 9] JP-A-2008-279056
[Patent Literature 10] International Publication No. 05/087675
[Patent Literature 11] JP-A-2008-214131
[Patent Literature 12] JP-A-07-48142

DISCLOSURE OF INVENTION

Problems to be Solved by the Invention

The object of the invention is to provide antimicrobial glass for water processing having a solubility with which the effective duration can be easily detected when used in an appropriate amount in home and a granular antimicrobial agent for water processing which has sufficient water permeability, antimicrobial effect, and service life, and, furthermore, an excellent filling processability when used for water processing in home.

Means for Solving the Problems

As a result of thorough studies for solving the above problems, the present inventors found that a granular antimicrobial agent for water processing which has a solubility at 25° C. of preferably 0.1 mg/g·L·hour to 1 mg/g·L·hour, comprises 0.5 wt % to 4 wt % of $Ag_2O$, 2 wt % to 10 wt % of $K_2O$, 35 wt % to 50 wt % of $SiO_2$, and 40 wt % to 55 wt % of $B_2O_3$, and has a semispherical or conical shape in part can be used. In addition, the inventors found that the antimicrobial agent is highly suitable for use in various kinds of water processing, particularly, the antimicrobial treatment of water used for washing, and completed the invention.

DESCRIPTION OF EMBODIMENTS

Hereinafter, the invention will be described. Moreover, % indicates % by weight (wt %).

The granular antimicrobial agent for water processing of the invention is consisted of water-soluble antimicrobial glass particles, and the solubility in deionized water at 25° C. is within a range of 0.1 mg/g·L·hour to 1 mg/g·L·hour. The antimicrobial agent of the invention has an advantage that the granular antimicrobial agent itself is dissolved according to the frequency of use (duration, the number of times, or the like) so as to reduce the weight of the antimicrobial agent, and the service life of the antimicrobial agent can be detected by observing the weight according to measurement by hand and the reduction in the bulk through visual inspection. The measurement by hand refers to estimation of the weight or bulk of the agent held in the hands. The granular antimicrobial agent for water processing of the invention is designed to show the effective duration of the antimicrobial power of water processing through weight changes that can be felt by the hands or changes in bulk that can be visually observed.

Considering general applications to expandable supplies in the home, such as the provision of microbe resistance and deodorization of water used for washing, the provision of microbe resistance to bathwater, and the inhibition of algae growth in a water tank, the amount of water for which the antimicrobial agent is used in the home is often several tens of liters to several hundreds of liters per cycle, and the temperature range of use is 0° C. to 45° C. When 1 g or less of the antimicrobial agent is used in total at this time, the amount is too small since the antimicrobial agent cannot be located, or it is difficult to determine changes that show the effective duration. On the other hand, when more than 100 g of the antimicrobial agent is used, the weight and bulk are too large, which causes obstacles and difficulties in using the agent, and therefore an antimicrobial agent that can exhibit sufficient antimicrobial properties for the above uses in an amount between 5 g to 100 g is preferred.

As an antimicrobial agent which can carry out an antimicrobial treatment of several tens of liters to several hundreds of liters of water per cycle in an amount between 5 g to 100 g and for which the amount of reduction is easily detected by measuring by hand, or the amount of reduction of the bulk is easily detected visually, there is silver glass having a dissolved amount of the glass (solubility) of 0.1 mg/g·L·hour to 1 mg/g·L·hour. The unit mg/g·L·hour indicates the weight lost by elution from 1 g of the antimicrobial agent per hour and liter of water. Specifically, in a case in which 50 g of the antimicrobial agent having a solubility of 0.1 mg/g·L·hour to 1 mg/g·L·hour is used, and the water amount is 50 liters, the antimicrobial agent is reduced at 0.25 g/hour to 2.5 g/hour, and therefore, when an antimicrobial treatment is carried out on 50 liters of water in one hour of washing per day, it is considered that 0.5% to 5% of the antimicrobial agent is lost per cycle, and the cumulative amount of the antimicrobial agent reduced in several tens of cycles can be easily determined by measuring by hand or visual observation.

Some antimicrobial glass particles are dissolved and break down so as to generate particulates or are solidified as a whole after having become wet once; however, in this case, it is not always possible to easily determine the amount of reduction by measuring by hand or visual observation, the generation of particulates makes the elution amount larger than the originally designed value, and an excessive amount of silver ions causes coloration contamination or precipitation, or particle solidification reduces the water permeable amount or elution amount, and sufficient antimicrobial properties may not be obtained, which is not preferred.

Meanwhile, the same antimicrobial agent may have different solubilities depending on the temperature, ionic strength, pH, and the like of water, but it is possible to use, for example, the solubility measured in deionized water at 25° C. as the evaluation standard of the dissolution susceptibility of the antimicrobial agent.

The glass composition of the granular antimicrobial agent for water processing in the invention contains 0.5 wt % to 4 wt % of $Ag_2O$, 2 wt % to 10 wt % of $K_2O$, 35 wt % to 50 wt % of $SiO_2$, and 40 wt % to 55 wt % of $B_2O_3$. $Ag_2O$, which is an antimicrobial properties-developing component, requires the use of a large amount of a vitreous antimicrobial agent in order to obtain the antimicrobial effect at 0.5% or less, and is not easily dissolved in the glass and precipitated as metallic silver at 4% or more, and therefore $Ag_2O$ is present at 0.5 wt % to 4 wt %, preferably at 1% to 3%, and more preferably at 1.5% to 2.5%.

$K_2O$, which acts as a component for adjusting the solubility of the glass, can control the solubility of the glass over a long period more easily than other alkali metals, and the content thereof is preferably 2 wt % to 10 wt %, more preferably 3% to 9%, and even more preferably 5% to 8%. The ratio of $SiO_2$ and $B_2O_3$ for forming the skeleton structure of the glass controls the solubility of the glass, in which the solubility is degraded when the fraction of $SiO_2$ is increased, and the solubility is improved when the fraction of $B_2O_3$ is increased. The content ratio of $SiO_2$ is preferably 38% to 50%, more preferably 40% to 49%, and particularly preferably 42% to 48%. The content ratio of $B_2O_3$ is preferably 42% to 55%, more preferably 43% to 53%, and particularly preferably 44% to 49%. Other components, such as Na, Al, Ca, Ba, Zn, and Co, may be mixed in as long as the amounts thereof are too small to affect the solubility of the glass over a long period. In addition, glass comprising $P_2O_5$ in the composition is easily turned into glass, but has a poor water resistance, and therefore the glass composition of the granular antimicrobial agent for water processing of the invention preferably does not comprise $P_2O_5$.

The granular antimicrobial agent for water processing of the invention preferably has a semispherical or conical shape in part, and has a bulk specific gravity of 0.9 g/mL to 1.1 g/mL. Generally, in an industrial method of manufacturing granular glass at a low cost, high-temperature liquid glass dissolved by heating is put into water so as to be quenched and made into amorphously crushed cullet, or passed through metal rollers so as to be made into a sheet shape (flake shape). However, for cullet, adjustment of the granularity is difficult, and particulates or coarse particles may be included, and therefore crushing or classification is required. In addition, since residual stress is present on the surface, fine cracks may easily occur, and since crushing propagates from the cracked portions during use, it is reported that fragments or dust are generated, and the granularity is easily altered. When coarse particles and particulates are mixed with each other, the bulk density is increased such that the water permeability is extremely degraded. On the other hand, a uniform granularity is achieved with flakes more easily than with cullet, but it is still not sufficient, and there are a lot of cracked sheet-molded glass fragments, and therefore it is dangerous to use flakes in the home. In addition, flakes also have a problem of degrading the water permeability since flat sheets are piled up. The granular antimicrobial agent for water processing of the invention preferably has a semispherical or conical shape in part. Having a semispherical or conical shape in part facilitates the control of the granularity and weight. The shape of the opposite surface to the semispherical or conical swelling is not limited, but is preferably planar from the viewpoint of easy manufacturing.

Since the antimicrobial agent of the invention has a semispherical or conical shape in at least one surface, unlike the flake shape, adhesion and overlapping of the planar surfaces of a number of particles hardly occur, the water permeability is excellent, the particles are not easily cracked due to the presence of roundness in the particles, the particles are not crushed even when being kneaded in a washing machine, particulates are not easily generated, and the risk is also low. Meanwhile, in comparison to molten spherical glass, such as glass beads, it is possible to manufacture the antimicrobial agent industrially at a low cost.

In a case in which the granular antimicrobial agent for water processing of the invention has a semispherical or conical shape, the maximum diameter at the bottom is preferably 2 mm to 8 mm, and the height is preferably 1 mm to 5 mm. The diameter is preferably 2.5 mm to 7 mm, and more preferably 3 mm to 6 mm for ease of cooling after the melting of the glass. When the diameter is 2 mm or less, the particles are too fine, and thus there are concerns that it may become difficult to maintain a sufficient granularity and the water permeability may be degraded. When the diameter is 8 mm or more, the granularity is excessively increased, and thus there is an effect that the solubility is degraded. Meanwhile, the height is also preferably 1 mm to 4 mm, and more preferably 1.5 mm to 3 mm for ease of cooling after the melting of the glass. When the height is 1 mm or less, the particles are too thin, and thus there are concerns that it may become difficult to maintain a sufficient granularity and the water permeability may be degraded. When the height is 5 mm or more, the granularity is excessively increased, and thus there is an effect that the solubility is degraded. The dimensional ratio of the height to the bottom maximum diameter (height/bottom maximum diameter) is preferably within 0.1 to 1.5, more preferably 0.2 to 1.2, and particularly preferably in a range of 0.3 to 0.9.

As the definition of the semispherical or conical shape, the cross section of the semispherical or conical shape does not need to be a perfect circle, and may be oval or polygonal since the water permeability is not impaired, which matches the object of the invention. The semispherical or conical shape includes a triangular pyramid shape or a subulate shape with a star-form cross section for designability, and also includes shapes having a groove or hole.

In addition, the granular antimicrobial agent for water processing of the invention is preferably manufactured by molding fused antimicrobial glass for water processing with cooling-molding rollers, and the granular antimicrobial agent for water processing of the invention can be preferably manufactured when the radius of curvature R of the top portion of the semispherical or conical shape of the granular antimicrobial agent for water processing is 0.1 d to 1.5 d with respect to the bottom maximum diameter d, and more preferably in a range of 0.2 d to 0.9 d since the particles are easily released from the rollers.

The preferred average weight of the granular antimicrobial agent for water processing of the invention per particle is 0.5 g to 2.0 g. When the average weight per particle is less than 0.5 g, the average weight is too small, and thus there is a possibility that the water permeability may be degraded. On the other hand, when several tens of grams of the granular antimicrobial agent for water processing having an average weight of greater than 2.0 g are filled into a bag using an automatic filling machine, the variation in the filled amount becomes large. In addition, a lower standard deviation in the weight of the granular antimicrobial agent for water processing is more favorable, and the standard deviation is preferably $\frac{1}{10}$ or less of an average weight due to stable solubility or a decrease in the variation of the filled amount.

The preferred bulk specific gravity of the granular antimicrobial agent for water processing of the invention is 0.9 g/mL to 1.1 g/mL. Considering that the water permeability can be obtained when several tens of grams of the granular antimicrobial agent for water processing of the invention are used, the contact duration is not sufficient at a bulk specific gravity of less than 0.9 g/mL, and the particles are filled too densely at a bulk specific gravity of greater than 1.1 g/mL such that the water permeability cannot be obtained sufficiently.

The granular antimicrobial agent for water processing used in the invention can be manufactured by mixing well compounds containing the necessary components, such as oxides, hydroxides, borates, chlorides, nitrates, sulfates, and carbonates, with a predetermined mixed amount, then heating and melting the mixture in a melting pot, and quenching the mixture.

In order to increase the cooling effect and adjust the shape and granularity of the granular antimicrobial agent for water processing of the invention, it is necessary to increase the contact area between the molten article and the coolant. For example, when the molten article of the glass is passed through two rolling metal cooling-molding rollers, which are cooled using a coolant, such as water, at a high speed, an extremely strong cooling effect can be obtained, and use of this cooling method facilitates the production of glass having an adjusted shape and granularity. Provision of semispherical or conical dents on at least one surface of the cooling-molding rollers can produce a glass granular article having a semispherical or conical shape in part and a narrow granularity.

The interval between two adjacent semispherical or conical dents on the surface of the cooling-molding roller is preferably 0.5 mm to 2.5 mm. When the interval is less than 0.5 mm, crushing becomes difficult, and thus it becomes difficult to obtain an even granularity, and when the interval is greater than 2.5 mm, planar portions being crushed are increased, which causes irregularities in the shape or granularity which is a feature of the granular vitreous antimicrobial agent of the invention. The reason why the shape is limited to a conical or semispherical shape is because the glass can be easily released from the rollers in such a shape. The glass in other shapes remains in the frame of the roller during production, and thus molding defects are easy to occur. When the glass is cooled by this method, the glass removed from the rollers has a thin sheet shape at sites that are not molded into semispherical or conical shape, and is easily fractured so that it is not necessary to control the granularity using crushing or classification, whereby a water-processing granular antimicrobial agent can be produced at low production costs without any loss.

Figure 3:
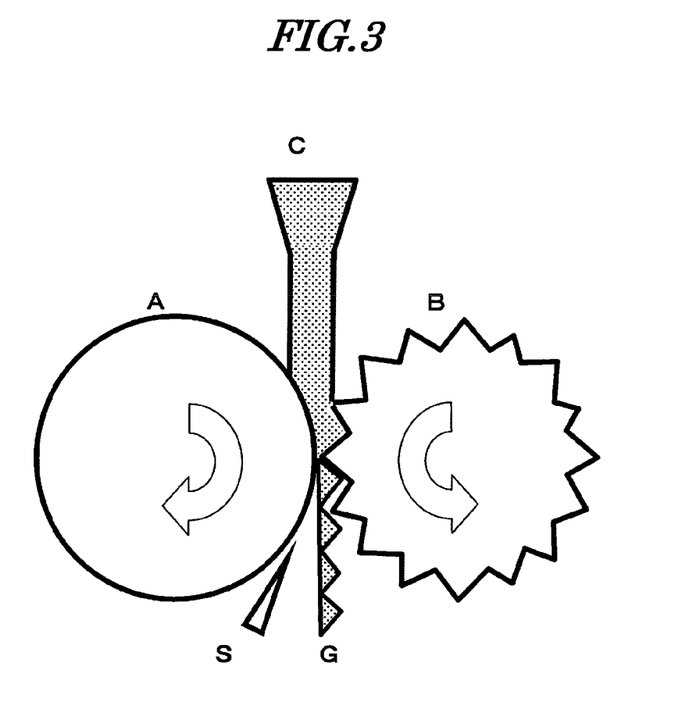
FIG. 3 shows an example of a method of manufacturing the granular antimicrobial agent for water processing of the invention using cooling-molding rollers.

The semispherical or conical dents may be provided at both of the two facing cooling-molding rollers, but extremely slight deviation between the two rollers during continuous operation causes deviation between the semispherical or conical portions present on both surfaces, whereby there is a concern of failure in producing a granular article having a constant shape, and, furthermore, crushing also becomes difficult. Use of cooling-molding rollers having a flat surface at one roller and dents at the other roller as shown in FIG. 3 is particularly preferable. In a case in which only one roller has dents, there is no protrusion on the surface even when molded particles remain on the dent side, and therefore no problem is caused even when the particles are sandwiched again in a gap. The roller on the flat side is preferably attached a scraper (S in FIG. 3), because it is possible to prevent the molded particles from adhering and remaining.

As the gap between the two facing cooling-molding rollers is narrowed, a thin sheet of glass remaining between the molded particles in the form of a "burr" becomes thinner, and the molded particles are more easily released, which is preferable; however, if the thin sheet becomes excessively thin, a burden is imposed on the apparatus. The gap is preferably 0.1 mm to 1.5 mm, and more preferably 0.3 mm to 1.0 mm.

While the molded particles that have passed through the cooling-molding rollers are separated into particles to a certain extent due to an impact of dropping or the like by their own weight, it is preferable to add an additional impact, such as vibration, and carry out a light crushing treatment so as to separate the particles into a granular shape, and, furthermore, according to the case, remove burrs present at the surroundings of the semispherical or conical shapes using a ball mill so as to use the particles that are made into a shape with no sharp edges.

A granular antimicrobial agent for water processing obtained in the above manner provides excellent water permeability and developing properties of the antimicrobial effect by adjustment of the solubility, shape, and granularity, and exhibits an effect of efficiently reducing the number of microbes included in water by either allowing passage of the water that is to undergo an antimicrobial treatment or dipping in the water that is to undergo an antimicrobial treatment. In addition, the antimicrobial glass itself is dissolved, and the amount thereof is reduced, whereby anyone can readily ascertain the effective duration of the antimicrobial effect. The antimicrobial glass of the invention can be particularly preferably used for antimicrobial treatments of water used for washing.

The granular antimicrobial agent for water processing of the invention provides its effect by being washed together with laundry, such as clothes, during ordinary washing, but still can provide the antimicrobial effect even when used singly without a detergent. In addition, the granular antimicrobial agent for water processing of the invention can be used with chemicals other than a detergent, such as a softener, a whitener, a deodorant, an ultraviolet absorber, and a fluorescent brightener.

The type of usage of the granular antimicrobial agent for water processing of the invention is not particularly limited, and still can be used in the original granular shape; however, when the agent is used for water processing, it is preferable to fill and pack preferably 5 g to 100 g, and more preferably several tens of grams of the agent in a non-woven fabric, net, water-permeable cartridge, or the like and use the agent. The non-woven fabric or net forms a bag shape, but the preferred size of the bag is a size that allows easy detection of the weight change by measuring by hand. Specifically, the vertical and horizontal widths are preferably in a range of 5 cm to 10 cm, and the thickness is not limited. However, packing tightly during packing so as to decrease void is preferred since the weight change can be detected by measuring by hand. In addition, the agent is preferably double-packed with a non-woven fabric and a net. The inside of the double packing is preferably a non-woven fabric with a fine mesh for preventing leakage of the antimicrobial agent, and the outside is preferably a net shape that is robust and can easily allow passage of water since the object of the outside is to maintain the strength of the non-woven fabric. A hydrophilic material that can allow passage of water into the non-woven fabric within a short time after the contact with water so that the antimicrobial agent packed in the non-woven fabric begins to be dissolved immediately after being immersed in water or allowing passage of water is preferable as the material of the inside non-woven fabric, and specific examples thereof include nylons and polyesters.

Use of an automatic measuring, filling, and wrapping machine for filling makes industrial mass production possible. Since the antimicrobial agent has a granular shape, mass measuring-type measurement can be used, but when an antimicrobial agent has a cullet form or a flake shape like the conventional art, particulates or the sharp portions of particles are stuck in a measurement operation portion, and there are cases in which the machine stops, leading to problems. Since the conical or semispherical granular antimicrobial agent for water processing has few particulates or sharply shaped articles, it is possible to produce without stopping an automatic measuring, filling, and wrapping machine.

Usage

The granular antimicrobial agent for water processing of the invention can be used for water processing in a variety of fields that require inhibition of the growth of fungus and algae, and microbe resistance, that is, electric appliances, toiletry products, toys, and the like.

More specific examples of the use include dishwashers, refrigerators, washing machines, pots, rice cookers, air conditioners, air cleaners, dehumidifiers, humidifiers, and the like as the electric appliances, toilet water, bathtubs, bathrooms, chamber pots, sanitary boxes, and bathtub lids as the toiletry products, and water guns, bath toys, cooking toys, and the like as the toys. Other uses include pools, tanks, water cisterns, antimicrobial sprays, and the like.

In comparison to the antimicrobial agents of the conventional art having a cullet shape, a flake shape, or a constant shape produced by fusion molding, the granular antimicrobial agent for water processing of the invention has excellent water permeability, microbe resistance, and filling properties, is also excellent in terms of the productivity or production costs, and allows the effective duration (service life) to be easily ascertained, and therefore the agent can be preferably used as an antimicrobial agent for various kinds of water processing, particularly washing.

EXAMPLES

Hereinafter, the invention will be described using examples, but the invention is not limited thereto.

The bulk specific gravity was measured by the graduated cylinder method in which a 100 mL graduated cylinder was used and tapping, which is dropping from a height of 1 cm, was carried out 50 times, and calculated as a weight per unit volume (unit gram/mL).

The solubility in Table 1 was obtained by feeding 1 g of the antimicrobial agent particles into 1 L of deionized water at 25° C., stirring the solution at 300 rpm for one hour, recovering the antimicrobial agent using a membrane filter, drying the recovered antimicrobial agent at 150° C. for 3 hours, measuring the weight reduction of the antimicrobial agent from before the feeding, and calculating the weight reduction of the antimicrobial agent with respect to 1 g of the weight of the original antimicrobial agent, 1 L of the deionized water, and 1 hour of dissolution period in a milligram unit.

Examples 1 to 4

Preparation of the Granular Antimicrobial Agent for Water Processing

Glass raw material mixtures having the compositions of Examples 1 to 4 as shown in Table 1 were heated and melted at 1,200° C. Meanwhile, the glass compositions (wt %) in Table 1 are indications of the weight ratios of the respective components of the glass raw material in a total weight ratio of the glass components of 100%. After being melted, the mixtures were cooled and molded using metal cooling-molding rollers having conical dents disposed on one surface, in which the cone had a diameter of 4 mm, a height of 2 mm, and a radius of curvature at the top portion of 1 mm, with an inter-roller gap of 0.5 mm, the obtained glass was simply hit and crushed, furthermore, the glass was dry-crushed for 10 minutes with alumina balls by ball milling, and then fine powders were screened and removed using a 1 mm-mesh metal net, thereby producing Examples 1 to 4 of the granular antimicrobial agent for water processing. In the molding process using the cooling-molding rollers, while a total amount of 200 kg of glass was molded, there was no particle which turned around without being separated from the roller with the dents and no particle which came into contact with a scraper in the planar surface roller, all the particles were connected with each other in a sheet shape, discharged from the gap between the rollers, dropped by their own weight, and divided into small specimens including approximately several tens to several hundreds of particles.

In addition, after a glass raw material mixture having the composition of Example 5 as shown in Table 1 was heated and melted at 1,200° C., the granular antimicrobial agent for water processing of Example 5 was obtained through the same operations as in Example 1 except that the mixture was cooled and molded using metal cooling-molding rollers having semispherical dents disposed on one surface, in which the semisphere had a diameter of 4 mm, a height of 2 mm, and a radius of curvature at the top portion of 2 mm. The bulk specific gravities of the obtained antimicrobial agents, the average weight and standard deviation of an arbitrary 10 particles, the solubilities, and the filling properties evaluated using an automatic filling machine are shown in Table 1. In the molding process using the cooling-molding rollers, while a total amount of 200 kg of glass was molded, there were several particles which turned around without being separated from the roller with the dents, but there was no error in the apparatus, and the particles were separated and dropped at the second turn. In addition, there was no particle which came into contact with a scraper in the planar surface roller, almost all of the particles were connected with each other in a sheet shape, discharged from the gap between the rollers, dropped by their own weight, and divided into small specimens including about several tens to several hundreds of particles.

Example 6

Preparation of the Granular Antimicrobial Agent for Water Processing

A glass raw material mixture having the composition of Example 6 as shown in Table 1 was heated and melted at 1,200° C., and a granular antimicrobial agent of Example 6 of the granular antimicrobial agent for water processing was obtained by the same method as in Example 1.

Comparative Examples 1 to 9

In Comparative Examples 1 and 2, flake-shaped vitreous antimicrobial agents were obtained by the same method as in Examples 1 and 2 except that the mixtures were cooled using metal rollers having no dent after being melted at 1,200° C. In addition, in Comparative Examples 3 and 4, flake-shaped vitreous antimicrobial agents were obtained by the same method as in Examples 1 and 2 except that the ratios of $SiO_2$ to $B_2O_3$ were different, and the mixtures were cooled using metal rollers having no dents after being melted at 1,200° C., and in Comparative Example 1, the granularity was adjusted to 5.6 mm to 9.5 mm using a sieve. In Comparative Examples 1 to 4, two metal rollers with no dent were used, scrapers were attached to both rollers, and the gap was 0.9 mm. The cooled glass was connected in a sheet shape, discharged from the gap between the rollers, occasionally broken and dropped by its own weight, but there were no determined sites to be divided, and thus the glass was frequently hit, divided into small specimens, and recovered.

In Comparative Examples 5 and 6, cullet-shaped vitreous antimicrobial agents were obtained by the same method as in Examples 1 and 2 except that the mixtures were directly cooled by water without using metal rollers after being melted at 1,200° C. In Comparative Examples 7 to 9, conical vitreous antimicrobial agents were obtained by the same method as in Example 1 except that a glass raw material mixture having the glass composition as shown in Table 1 was used. The original composition of each glass and the solubility of the antimicrobial particles are shown in Table 1, and the bulk specific gravities of the obtained antimicrobial agents, the average weight and standard deviation of an arbitrary 10 particles, the solubilities, and the filling properties evaluated using an automatic filling machine are shown in Table 2.

TABLE 1

| | Glass composition (wt %) | | | | | Solubility |
|---|---|---|---|---|---|---|
| | $Ag_2O$ | $K_2O$ | $Na_2O$ | $SiO_2$ | $B_2O_3$ | (mg/g · L · H) |
| Example 1 | 2.0 | 6.0 | 0.0 | 45.0 | 47.0 | 0.38 |
| Example 2 | 1.9 | 8.8 | 0.0 | 41.1 | 48.2 | 0.48 |
| Example 3 | 0.8 | 8.8 | 0.0 | 41.0 | 49.4 | 0.48 |
| Example 4 | 3.8 | 7.0 | 0.0 | 42.0 | 47.2 | 0.40 |
| Example 5 | 2.0 | 6.0 | 0.0 | 45.0 | 47.0 | 0.34 |
| Example 6 | 2.0 | 2.0 | 0.0 | 45.6 | 50.4 | 0.18 |
| Comparative Example 1 | 2.0 | 6.0 | 0.0 | 45.0 | 47.0 | 1.98 |
| Comparative Example 2 | 1.9 | 8.8 | 0.0 | 41.1 | 48.2 | 2.08 |
| Comparative Example 3 | 2.0 | 6.0 | 0.0 | 55.0 | 37.0 | 0.08 |
| Comparative Example 4 | 1.9 | 8.8 | 0.0 | 29.1 | 60.2 | 2.08 |
| Comparative Example 5 | 2.0 | 6.0 | 0.0 | 50.5 | 41.5 | 0.18 |
| Comparative Example 6 | 1.9 | 8.8 | 0.0 | 34.1 | 55.2 | 1.40 |
| Comparative Example 7 | 0.4 | 6.0 | 0.0 | 46.6 | 47.0 | 0.96 |
| Comparative Example 8 | 4.3 | 8.8 | 0.0 | 38.7 | 48.2 | 0.04 |
| Comparative Example 9 | 2.0 | 0.0 | 6.0 | 45.0 | 47.0 | 0.02 |

TABLE 2

| | Shape | Bulk specific gravity (g/mL) | Average weight (g) | Standard deviation | Filling properties |
|---|---|---|---|---|---|
| Example 1 | Cone | 1.03 | 0.68 | 0.018 | Good |
| Example 2 | Cone | 1.05 | 0.78 | 0.059 | Good |
| Example 3 | Cone | 1.05 | 0.88 | 0.044 | Good |
| Example 4 | Cone | 1.00 | 0.69 | 0.032 | Good |
| Example 5 | Semisphere | 1.00 | 1.11 | 0.022 | Good |
| Example 6 | Cone | 1.03 | 0.76 | 0.041 | Good |
| Comparative Example 1 | Flake | 1.09 | 0.08 | 0.010 | Poor |
| Comparative Example 2 | Flake | 1.24 | 0.04 | 0.020 | Poor |
| Comparative Example 3 | Flake | 1.23 | 0.03 | 0.020 | Poor |
| Comparative Example 4 | Flake | 1.22 | 0.04 | 0.020 | Poor |
| Comparative Example 5 | Cullet | 1.39 | 0.12 | 0.110 | Poor |
| Comparative Example 6 | Cullet | 0.98 | 0.01 | 0.010 | Poor |
| Comparative Example 7 | Cone | 1.02 | 0.66 | 0.033 | Good |
| Comparative Example 8 | Cone | 1.02 | 0.72 | 0.028 | Good |
| Comparative Example 9 | Cone | 1.01 | 0.78 | 0.041 | Good |

Washing Test (Microbe Resistance Test and Durability Determination)

50 g of each of Examples 1 to 6 and Comparative Examples 1 to 9 was packed in a 7 cm×7 cm bag-shaped nylon non-woven fabric, and double wrapped using a net, thereby producing Specimens 1 to 6 from Examples 1 to 6 and Specimens 7 to 15 from Comparative Examples 1 to 9. The specimen was embedded in a hose of a bath pump for domestic electric washing machines, and a water-passing test was carried out. The water permeability was evaluated as follows: a time period during which 50 L of water was pumped up to an electric washing machine from a basket that was placed on the floor and filled with tap water up to a certain water level was measured using a bath pump, and in a case in which an increase in the pumping-up period was 30% or less with respect to the pumping-up period when a blank specimen having no antimicrobial agent packed therein was embedded, the amount of water passed was evaluated as not degraded, and in a case in which an increase in the pumping-up period was larger than 30%, the amount of water passed was evaluated as degraded, and the evaluation results are shown in Table 3.

In addition, washing was carried out once after adding clothes, a 10 cm×10 cm polyester fabric, and any of Specimens 1 to 15 in a domestic electric washing machine not using a bath pump and directly using tap water, and the number of microbes attached to the polyester fabric was measured by the streak plate method in which an general agar medium was used. The percentages of the numbers of microbes when Specimens 1 to 15 were used with respect to the number of microbes when no specimen was used are shown in Table 3 as the microbe reduction rates (%). Furthermore, washing was carried out ten times with clothes and Specimens 1 to 15 in the domestic electric washing machine, and it was determined whether a change in the amount of reduction of the specimen could be detected by measuring by hand. Meanwhile, the change in the amount of reduction by measuring by hand was determined based not only on a change in the weight but also on the clogging state of the antimicrobial agent in the filled bag or the shaking state.

TABLE 3

| | Water permeability | Microbe reduction rate after 1$^{st}$ washing (%) | Detection of change in amount of reduction by measuring by hand |
|---|---|---|---|
| Example 1 | Not degraded | 99.7 | Possible |
| Example 2 | Not degraded | 99.9 | Possible |
| Example 3 | Not degraded | 99.9 | Possible |
| Example 4 | Not degraded | 99.9 | Possible |
| Example 5 | Not degraded | 99.9 | Possible |
| Example 6 | Not degraded | 98 | Possible |
| Comparative Example 1 | Degraded | 99.9 | Possible |
| Comparative Example 2 | Degraded | 99.9 | Possible |
| Comparative Example 3 | Degraded | 84 | Impossible |
| Comparative Example 4 | Degraded | 99.9 | Possible |
| Comparative Example 5 | Degraded | 78 | Impossible |
| Comparative Example 6 | Degraded | 99.9 | Possible |
| Comparative Example 7 | Not degraded | 24 | Possible |
| Comparative Example 8 | Not degraded | 98 | Impossible |
| Comparative Example 9 | Not degraded | 91 | Impossible |

In Examples 1 to 6, the bags filled with the antimicrobial agents could be easily held by the hands, and particles inside the bags were movable so that even a subtle amount of reduction could be easily detected from the clogging state or shaking state of the antimicrobial agent, whereas the bags filled with the flake and cullet-shaped antimicrobial agents of Comparative Examples 1 to 6 had poorly movable particles therein, and the feelings of the clogging state or shaking state of the antimicrobial agent varied with the holding sites, and therefore the change could not be detected when the change of weight was small.

As is clear from Table 3, the granular antimicrobial agent for water processing of the invention has both water permeability and microbe resistance, and has a high effect of reducing microbes included in water. In addition, it is possible to estimate the effective duration of the antimicrobial agent by measuring by hand. Example 6 containing a relatively small amount, 2%, of $K_2O$, which is a component for adjusting the solubility of the glass, had a low solubility, and also had a slightly low microbe reduction rate, but the other properties were satisfactory so that the antimicrobial agent can be used in practice. In addition, according to the measuring by hand, it seemed that Examples 2 and 3 were reduced slightly faster than Example 1, but the other performances were fully satisfactory.

Durability Detection Test 50 g of the granular antimicrobial agent of Example 1 was packed in a 7 cm×7 cm bag-shaped nylon non-woven fabric, and, furthermore, double wrapped using a net, thereby producing a specimen. Washing tests were carried out 40 times with clothes, a 10 cm×10 cm polyester fabric, and the specimen added to the domestic electric washing machine. The specimen was removed after every two times of the washing, and dried under vacuum at 60° C. for 2 hours, the weight was measured, the weight residual ratio W (unit: %) of the antimicrobial agent to the original weight (50 g) of the antimicrobial agent was calculated and shown in FIG. 4. In addition, the number of microbes attached to the polyester fabric was measured by the streak plate method in which an general agar medium was used, and the microbe reduction rate D (unit: %) as compared to a case in which no specimen was used in washing was calculated and shown in FIG. 4.

Figure 4:
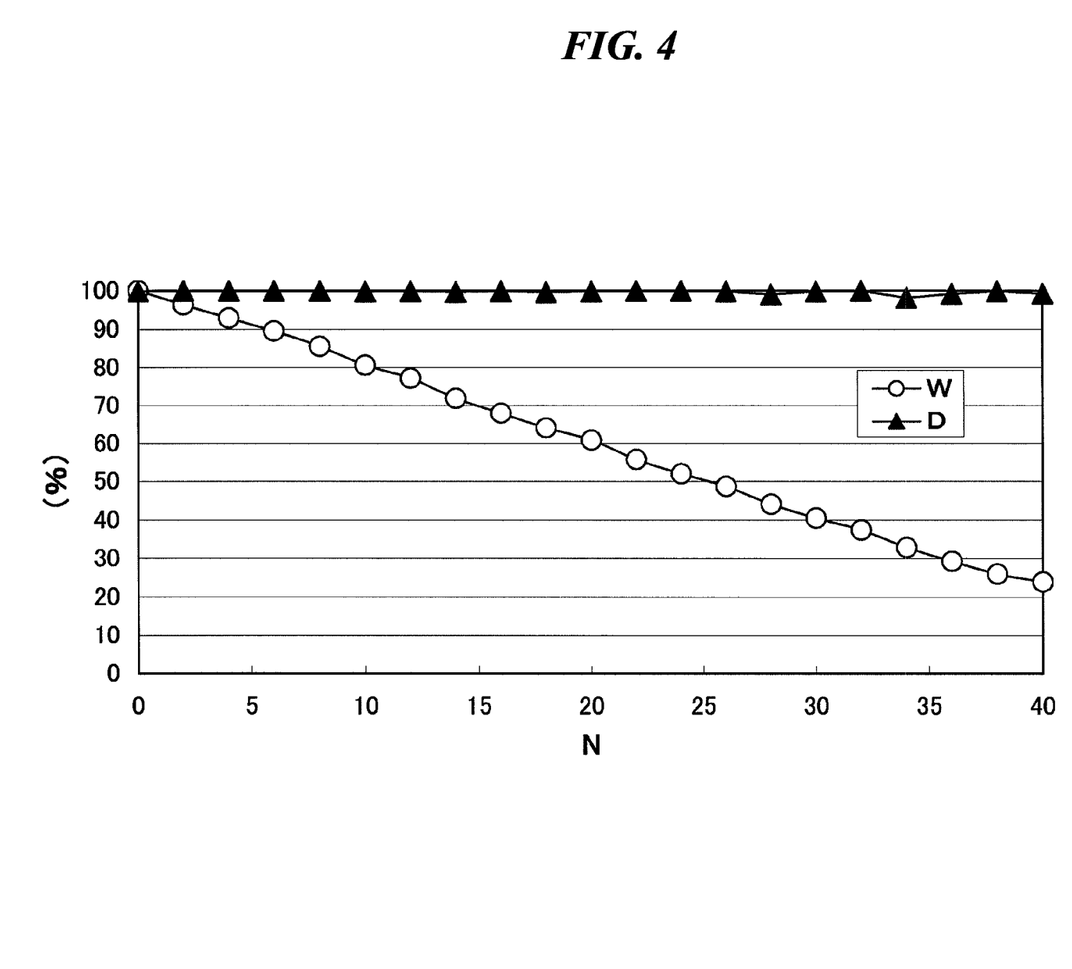
FIG. 4 shows the results of the effective duration detection test of the granular antimicrobial agent for water processing of the invention.

Meanwhile, the microbe reduction rate D follows the following formula. D becomes 100% when the number of microbes is zero in washing in which the antimicrobial agent is used, and D becomes 0% when there is no difference from the number of microbes when the antimicrobial agent is not used in washing.

Microbe reduction ratio $D$ (%)=100×(the number of microbes when the antimicrobial agent is not used in washing–the number of microbes when the antimicrobial agent is used in washing)/the number of microbes when the antimicrobial agent is not used in washing The antimicrobial agent for water processing of the invention maintained a high microbe reduction rate despite a decrease in the amount at least until the weight became ¼ of the original amount.

INDUSTRIAL APPLICABILITY

The antimicrobial agent for water processing of the invention is excellent in terms of the water permeability, excellently exhibits an antimicrobial effect, and either allows passage of water that is to undergo an antimicrobial treatment or is dipped in water that is to undergo an antimicrobial treatment so as to exhibit an effect of efficiently reducing the number of microbes included in the water. In addition, since the antimicrobial agent is dissolved and reduced to an appropriate extent, anyone can readily ascertain the effective duration of the antimicrobial effect. The granular antimicrobial agent for water processing of the invention can be particularly preferably used for antimicrobial treatments of water used for washing.

Figure 1:
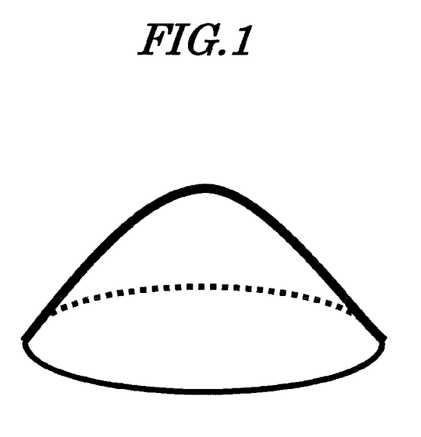
FIG. 1 shows the shape of the granular antimicrobial agent for water processing of the invention.
Figure 2:
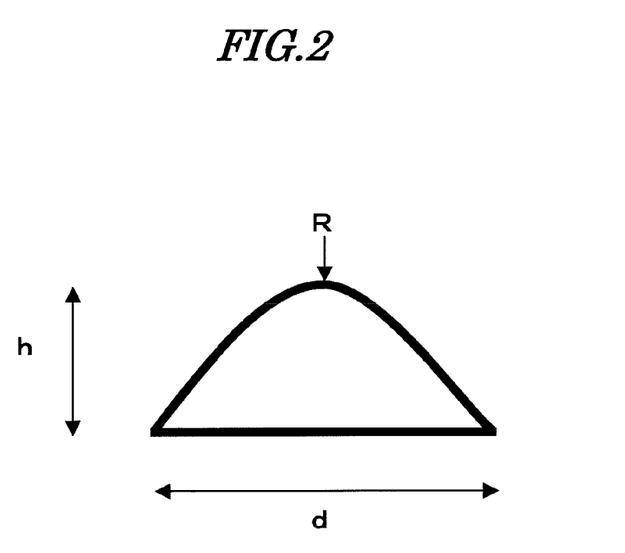
FIG. 2 shows the dimensions of the shape of the granular antimicrobial agent for water processing of the invention.

REFERENCE NUMERALS h indicates the height of the conical antimicrobial agent of the invention in FIG. 2.

d indicates the diameter of the bottom of the conical antimicrobial agent of the invention in FIG. 2.

R indicates the radius of curvature at the top portion of the conical antimicrobial agent of the invention in FIG. 2.

A is the cooling-molding roller (planar surface) of the glass in FIG. 3.

B is the cooling-molding roller (having dents) of the glass in FIG. 3.

C is fused glass in FIG. 3.

S is the scraper in FIG. 3.

G is glass shaped into a conical shape.

N is the number of times of washing in the durability detection test (FIG. 4) (horizontal axis unit: number of times).

D is the microbe reduction rate in the durability detection test (FIG. 4) (vertical axis unit: %).

W is the mass residual rate of the antimicrobial agent in the durability detection test (FIG. 4) (vertical axis unit: %).

What is claimed is:

1. A granular antimicrobial agent for water processing comprising 0.5 wt % to 4 wt % of $Ag_2O$, 2 wt % to 10 wt % of $K_2O$, 35 wt % to 50 wt % of $SiO_2$, and 40 wt % to 55 wt % of $B_2O_3$,
 wherein the solubility of the granular antimicrobial agent at 25° C. is within a range of 0.1 mg/g·L·hour to 1 mg/g·L·hour;
 wherein the composition does not comprise $P_2O_5$;
 wherein the bulk specific gravity of the granular antimicrobial agent is between 0.9 g/mL and 1.1 g/mL;
 wherein the average weight per particle of the granular antimicrobial agent is between 0.5 g and 2.0 g; and
 wherein at least one surface of the granular antimicrobial agent has a conical shape, and the maximum diameter at the bottom of the granular antimicrobial agent is 2 mm to 8 mm.

2. The granular antimicrobial agent for water processing according to claim 1, wherein the dimensional ratio of the height to the bottom maximum diameter is between 0.1 and 1.5.

3. The granular antimicrobial agent for water processing according to claim 1, wherein the height is 1 mm to 4 mm.

4. The granular antimicrobial agent for water processing according to claim 1, wherein the radius of curvature R of the top portion of the conical shape is 0.1 d to 1.5 d with respect to the bottom maximum diameter d.

5. A method of manufacturing the granular antimicrobial agent for water processing according to claim 1, wherein a cooling-molding roller having dents on the surface is used.

6. The method according to claim 5, wherein cooling-molding rollers having a flat surface at one roller and dents at the other roller is used.

7. The method according to claim 5, wherein the interval between two adjacent dents on the surface of the cooling-molding roller is 0.5 mm to 2.5 mm.

8. The method according to claim 6, wherein the gap between the two facing cooling-molding rollers is 0.1 mm to 1.5 mm.

9. A washing antimicrobial agent product, wherein the granular antimicrobial agent for water processing according to claim 1 is filled in water-permeable wrapping in a range of 5 g to 100 g.

10. The washing antimicrobial agent product according to claim 9, wherein the wrapping has a dual structure composed of a water-permeable non-woven fabric inside bag and a water-permeable outside bag.

* * * * *